United States Patent [19]
Forner et al.

[11] Patent Number: 5,656,601
[45] Date of Patent: Aug. 12, 1997

[54] ACYLATED SPLENOPENTINS, METHODS FOR THEIR SYNTHESIS AND THEIR USE

[75] Inventors: Klaus Forner; Angelika Ehrlich; Wolfgang Diezel; Rolf Eckert; Elke Euthin; Eberhard Krause; Peter Slonina; Hans-Dieter Volk; Heinrich Repke; Monika Georgi; Martina Leidert; Michael Bienert, all of Berlin, Germany; Michail Ovcinnikov, Moskau, U.S.S.R.; Ralph Schmidt; Manfred Schuett, both of Berlin, Germany; Renate Mentel, Greifswald; Winfried Breustedt, Berlin, both of Germany

[73] Assignee: Berlin-Chemie AG, Berlin, Germany

[21] Appl. No.: 721,902

[22] Filed: Jun. 20, 1991

(Under 37 CFR 1.47)

Related U.S. Application Data

[63] Continuation-in-part of Ser. No. 209,252, Jun. 20, 1988, abandoned.

[30] Foreign Application Priority Data

| Jun. 19, 1987 | [DD] | German Dem. Rep. | WPC07K/3039755 |
| Dec. 23, 1987 | [DD] | German Dem. Rep. | WPC07K/3110802 |
| Jan. 8, 1988 | [DD] | German Dem. Rep. | WPA61K/3121444 |
| Mar. 31, 1988 | [DD] | German Dem. Rep. | WPA61K/3143128 |

[51] Int. Cl.$^6$ .............. A61K 38/08; C07K 7/06
[52] U.S. Cl. .............. 514/17; 514/15; 530/323; 530/324; 530/325; 530/326; 530/327; 530/330
[58] Field of Search ............ 530/323, 324, 530/325, 326, 327, 330; 514/15, 17

[56] References Cited

U.S. PATENT DOCUMENTS

| 4,190,646 | 2/1980 | Goldstein | 424/177 |
| 4,298,523 | 11/1981 | Heavner | 514/17 |
| 4,505,853 | 3/1985 | Goldstein | 514/17 |
| 4,629,723 | 12/1986 | Goldstein | 514/17 |

OTHER PUBLICATIONS

Burger, A. "A guide to the chemical basis of drug design" John Wiley & Sons, 1984, p. 15.
Diezel et al "Induction of augmentation of mitogen induced immune interferon production" CA 101: 1894802 (1984).
Diezel et al "Effect of SP-5 on the antibody formation in immunosupressed mice" CA 105: 189020g (1986).
Heaver et al "Biological active Analysis of Thymopentin" Peptides 7 1015–1019 (1986).
Audhya et al "Contracting biological activities of thymopoietin and splenin" Pro. Natl. Acad. Sci. 81 2847–2849 (1984).
Heavner et al "Structural requirement for biological activity of thymopentin Analogs" Arch. Biochem Biophys. 242 248–255 (1985).

Diezel et al "Effect of splenopentin on antibody formation" Esp. Clin. Endocrinol. 87 215–8 (1986) Abstract & formula from Medline attached).
Notari "Biopharmaceutics and Pharmacokinetics" Marcel Dekker Inc. p. 216, 222 (1975).
"Functional effects of splenin 32–34 on antibody formation in immunosupressed mice", Biomed. Biochem. Acta 45 (1986) 10, 1349–1352, by W. Diezel et al.
"Histaminrezeptor–tragende Lymphozyten. III. Suppression von Immunreaktionen nach Abtoeten Histaminrezeptor–tragender Lymphozyten durch ein Konjugat aus Histamin und der A–Kette des Mistellektins I', Biomed. Biochim. Acta 44 (1985) 7/8, 1239–1245.
"Die experimentellen Verfahren zur Charakterisierung von Membranrezeptoren durch Radioligand–Bindungsstudien" and Quantitative Analyse der Ligand–Bindungskinetik Chapters 6 and 7 from German language treatise.
"The Generation and Regulation of Lymphocyte Populations", by Margrit P. Scheid et al, J. Exp. Med., 1727–1743, (1978).
"Monoclonal antibodies against rat mast cells differentiate between subtypes", Agents and Actions, vol. 20, 3/4 (1987), 216–218, by H. Repke et al.
"Muscarinic receptor–detergent complexes with different biochemical propertiew: selective solubilization, lectin affinity chromatography and ligand binding studies", Biochimica et Biophysica Acta, 929, (1987) 47–61, by Heinrich Repke.
"The Colony–to–cluster ratio in agar cultures of bone marrow. I. Constancy under standardized conditions and alteration in tumour–bearing mice and by various inhibitors added in vitro", Biomed. Biochim. Acta, 46, (1987) 7, 581–586, by Hildegunde Schunck et al.
"Kinetics of Specific IgE Antibody and Total IgE Responses in Mice: The Effect of Immunosuppressive Treatment", Int. Archs Allergy appl. Immun., 72: 16–21, (1983), by J. Wyczolkowska et al.
"Complete Amino Acid Sequences of Bovine Thymopoietins I, II, and III: Closely Homologous Polypeptides", Biochemistry, (1981), 20, 6195–6200, by Tapan Audhya et al.

(List continued on next page.)

*Primary Examiner*—Ceila Chang
*Attorney, Agent, or Firm*—Jordan and Hamburg

[57] ABSTRACT

The invention relates to new compounds of acylated splenopentins of Formula I

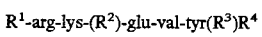

wherein $R^1$, $R^2$, $R^3$, $R^4$ are as defined in the specification, methods for their synthesis by acylation of splenopentins, as well as to their use as pharmacologically active peptides which are suitable for normalizing the function of the immunological system in primary and secondary immunological deficiencies.

3 Claims, 5 Drawing Sheets

OTHER PUBLICATIONS

"Inhibition of HIV–Associated Reverse Transcriptase by Sugar–Modified Derivatives of Thymidine 5'–Triphosphate in Comparison to Cellular DNA Polymerases α and β", Biochemical and Biophysical Research Communications, vol. 148, No. 1, (1987), 78–85, by E. Matthes et al.

Diezel et al. "Unduction and augmentation of mitogen–induced immune interferon production in human lymphocytes by a sunthetic thymopoietin pentapiptede": Biomed. biochim. Acta, v. 43, K9–K12 1984.

Virelizier et al. "Deficiencies of interferon production in children" EMBASE No. 84186869 1984.

Ecker et al. "Histamine receptor bearing lymphocytes HRL VIII . . . " BIOSIS No. 83076018.

ACYLATED SPLENOPENTINS, METHODS FOR THEIR SYNTHESIS AND THEIR USE

This application is a continuation-in-part of application Ser. No. 07/209,252, filed Jun. 20, 1988, abandoned.

BACKGROUND OF THE INVENTION

The invention is directed to new derivatives of the pentapeptide, splenopentin, arg-lys-glu-val-tyr, methods for their synthesis and purification, as well their use as immunobiologically active pharmaceutical preparations.

According to the present invention, splenopentin and its derivatives are used as immunological regulators in medical therapy. The field of application of the invention is the pharmaceutical industry.

As a result of extensive investigations of the isolation and characterization of peptides, which affect the immunological system, such materials as the thymopoietins and splenin (T. Audhya et al., Biochemistry 20, 6195 (1981)) have been isolated from the thymus or the spleen in recent years.

Although they originate from different organs, these peptides largely have a structural similarity. They consist of 49 amino acids and their sequence differs only in position 34 due to aspartic or glutamic acid. On the other hand, they differ clearly in their biological activity. For example, thymopoietins affect neuromuscular transmission (M.P. Scheid et al., J. Exp. med. 147, 1727 (1978)), stimulate the differentiation of early T cells and inhibit the differentiation of early B cells.

On the other hand, splenin stimulates the differentiation of T and B cells and has no neuroactivity. The biological activity of the splenin molecule as a whole is reproduced by its partial sequence 32–36, arg-lys-glu-val-tyr (splenopentin).

The synthesis of biologically active substances assumes to a constantly greater extent the simultaneous development of more highly sensitive and economically more effective chromatographic methods of purification. Of prime importance in this connection is the use of those methods, which have a high substance throughput, a uniformly good recovery rate and a high system resolution, when simple support and solvent systems are used.

Because of the slight charge and polarity differences of a large number of components, the chromatographic separation of differently acylated splenopentin peptides requires the use of more expensive and costly chromatographic techniques. Preferably, HPLC methods, based on reverse-phase silica gels, as well as method of polar adsorption and partition chromatography on normal silica gel phases are used.

According to the proposal of the DE 3 421 614 (1984), the chromatographic purification of splenopentins is carried out on normal-phase silica gel in methylene chloride-containing solvents. Furthermore, the proposal has already been made that the chromatographic separation of crude, synthetic splenopentin products be carried out by adsorption or partition chromatography on silica gel 60, using pyridine-containing organic solvents. Similar methods of separation are proposed in DE 2 804 566 (1977) for the purification of thymopentin or monoacetyl thymopentin.

It is a disadvantage of methods based on reverse-phase or normal-phase silica gel that the cost of the equipment and the material is high. This precludes their use for the production of large amounts of products of high purity. Moreover, the low capacity of the system, the low recovery rates due to nonspecific adsorption, as well as its inadequate ability to separate, are limiting factors for its application.

The usual ion exchange/chromatographic purification methods for peptides are characterized by the use of salts during the elution process. The chromatographic purification of nona- and decapeptides, described in DE 2,732,587 as well as in DE 2,617,646 is accomplished by the use of carboxymethylcellulose with elution agents containing sodium chloride or ammonium acetate. For purifying the substances, an expensive desalinization is therefore subsequently always necessary.

It is an object of the invention to develop new immunologically active derivatives of splenopentin (SP5) and methods for their synthesis and purification and to make immunologically effective pharmaceutical preparations available.

SUMMARY OF THE INVENTION

The inventive, new, acylated splenopentins (Ac-SP5) are compounds of formula I $$R^1\text{-arg-lys-}(R^2)\text{-gly-val-tyr}(R^3)R^4 \qquad \qquad I$$

in which
$R^1$ represents hydrogen, $C_1$ to $C_7$ alkyl, $C_6$ to $C_{12}$ aryl, $C_7$ to $C_{20}$ alkaryl, $C_7$ to $C_{20}$ aralkyl, $C_1$ to $C_{18}$ alkanoyl, $C_2$ to $C_7$ alkenyl, $C_2$ to $C_7$ alkynyl, $C_6$ to $C_{12}$ polyhydroxyalkanoyl, —$CO(CH_2)_n$—COOH (n = 1 to 8),
—$CO(CHOH)_n$—COOH (n = 1 to 12),
—CO—$(CH_2)_n$—CO-arg-lys-glu-val-tyr (n = 1 to 8),
—CO—$(CHOH)_n$—CO-arg-lys-glu-val-tyr (n = 1 to 12), $R^2$ represents hydrogen $C_1$ to $C_7$ alkyl, $C_6$ to $C_{12}$ aryl, $C_7$ to $C_{20}$ alkaryl, $C_1$ to $C_{18}$ alkanoyl, $C_2$ to $C_7$ alkenyl, $C_2$ to $C_7$ alkynyl, $C_6$ to $C_{12}$ polyhydroxyalkanoyl,
—$CO(CH_2)_n$—COOH (n = 1 to 8),
—$CO(CHOH)_n$—COOH (n = 1 to 12),
—$CO(CH_2)_n$—CO-($N^\epsilon$-lys)-glu-val-tyr (n = 1 to 8)
—$CO(CHOH)_n$—CO-(N-lys)-glu-val-tyr (n = 1 to 12), $R^3$ represents hydrogen, $C_1$ to $C_7$ alkyl, $C_6$ to $C_{12}$ aryl, $C_7$ to $C_{20}$ alkaryl, $C_1$ to $C_{18}$ alkanoyl, $C_2$ to $C_7$ alkenyl, $C_2$ to $C_7$ alkynyl and

$R^4$ represents OH, $NH_2$, $NHR^5$, $NR_2^5$, $OR^5$, wherein $R^5$ is $C_1$ to $C_{18}$ alkyl, $C_2$ to $C_7$ alkenyl, $C_2$ to $_7$ alkynyl $C_7$ to $C_{20}$ aralkyl, $C_7$ to $C_{20}$ alkaryl, —$(CHOH)_n$-polyhydroxyalkyl with n = 1 to 8,
—$(CH_2)_m$—NH-tyr-val-glu-lys-arg with m = 1 to 18
—$(CH_2CH_2$—$O)_m$-tyr-val-glu-lys-arg and
—$(CH_2CH_2$—$O)_m$—NH-tyr-val-glu-lys-arg with m = 1 to 10.

The terms aryl, alkaryl and aralkyl as used herein exclude heterocyclic compounds, i.e., are limited to homocyclic compounds. Excluded from the scope of the invention as defined by formula I is the unsubstituted compound, i.e., the compound in which $R_1$, $R_2$ and $R_3$ all are H and $R_4$ is OH. Also, it is a requirement of the invention that at least one of $R_1$, $R_2$ and $R_3$ be an acyl group. Particularly preferred compounds according to the invention are $N^\epsilon$-lys-monoacetyl splenopentin and $N^\alpha$-arg,$N^\epsilon$-lys-diacetyl splenopentin. The terms aryl, alkaryl and aralkyl as used herein exclude heterocyclic compounds, i.e., are limited to homocyclic compounds. Excluded from the scope of the invention as defined by formula I is the unsubstituted compound, i.e., the compound in which $R_1$, $R_2$ and $R_3$ all are H and $R_4$ is OH. Also, it is a requirement of the invention that at least one of $R_1$, $R_2$ and $R_3$ be an acyl group. Particularly preferred compounds according to the invention are $N^\epsilon$-lys-monoacetyl splenopentin and $N^\alpha$-arg,$N^\epsilon$-lys-diacetyl splenopentin.

Pursuant to the invention, the splenopentin derivatives are synthesized in such a manner that, if appropriate protective groups as well as different acylating reagents are used, a selective acylation is achieved of the N-position of the arginine and/or of the lysine and/or of the O-position of the tyrosine and the formation of by-products is avoided. Methods for acylating splenopentins have not been described previously. It has been ascertained that the use of conventional acylating agents, such as acetic anhydride and acid chloride, leads in a considerable measure to the formation of unwanted by-products (racemization at val and at tyr, glutarimide formation); during the synthesis of $N^\alpha$-arg- and $N^\epsilon$-lys-diacylated splenopentins (DAc-SP5), O-acyl-tyr by-products are formed. The reaction with p-nitrophenyl acetate also does not proceed without the formation of by-products. Moreover, the removal of the toxic p-nitrophenol formed especially from arginine-containing peptides, creates considerable difficulties. Pursuant to the invention, however, the selective acylation can be carried out successfully through the use of the appropriate N-hydroxy-norborn-5-ene-2,3-dicarboximide esters of carboxylic acids to form mono- (MAc-SP5) or diacyl-splenopentins (DAc-SP5). The synthesis of the acetyl compounds, the monoacetylated as well as of the diacetylated, succeeds advantageously due to the use of N-acetoxy-norborn-5-ene-2,3-dicarboximide (acetyl-ONB) (II) as well as of 1-acetoxy-benzotriazole (III).

Surprisingly, it has been ascertained that acetyl-ONB II, which was used for the very first time as acetylation agent, has special advantages. Because of its high resistance to hydrolysis, it has a very good shelf life and can be used for acylations in organic as well as in aqueous media; above all, it is advantageous because of its high reactivity with amino groups, even without the addition of base and in an extremely short time. The N-hydroxy-norborn-5-ene-2,3-dicarboximide, formed during the course of the reaction, can easily be removed and is not toxic, so that its use appears to be especially advantageous above all in the pharmaceutical industry.

With the help of this acylating agents, it is possible to synthesize the monoacyl and diacyl compounds in good yields (90% of the theoretical), while avoiding unwanted side reactions. If the acylation is carried out in the presence of tertiary amines, the corresponding triacyl compounds are obtained. The separation of the acylated splenopentins obtained can be accomplished particularly advantageously owing to the fact that the chromatographic separation on carboxylated cation exchangers is carried out in aqueous elution systems at an ionic strength between $10^{-2}$ and $10^{-5}$ moles/L. Suitable support materials are acrylic acid/divinylbenzene copolymers. At a high carrier capacity (5 to 10 mg peptide/mL of column volume), which is normal for ion exchange chromatography, the elution of the peptides, pursuant to the invention, proceeds isocratically with aqueous eluants, the necessary ionic strength between $10^{-2}$ and $10^{-5}$ moles/L being realized by the addition of acids, Triacetyl [$N^\alpha$-arg, $N^\epsilon$-lys, O-tyr]-splenopentin,
triacetyl [$N^\alpha$-arg, $N^\gamma$-arg, $N^2$-lys]-splenopentin,
diacetyl [$N^\alpha$-arg, $N^\epsilon$-lys]splenopentin,
mono [$N^\alpha$-arg]-splenopentin,
mono [$N^\epsilon$-lys]-splenopentin and the enantiomers
D-tyr-diacetyl [$N^\alpha$-arg, $N^\epsilon$-lys]-splenopentin and
L-tyr-diacetyl [$N^\alpha$-arg, $N^\epsilon$-lys]-splenopentin surprisingly are eluted with increasing $K^1$ values and, with that, separated according to their polarity. The recovery rate for all peptides separated is better than 95%.

Especially good separation effects are achieved if the eluant contains 10 to 20% ethanol. Because of the low ionic strength in the elution system, the peptides can be isolated simply and gently by concentrating the appropriate fractions and subsequently freeze drying. The purity of the isolated peptides, as determined by reverse phase HPLC, is better than 98%. Additional desalinization steps, necessary with other methods, are not required. Other advantages of the inventive system are the use of less expensive chromatographic support materials and the high degree of re-usability of the support (more than 100 chromatographic cycles).

By mixing the new compounds, so obtained, with pharmaceutically acceptable carrier materials and/or physiologically tolerated diluents, the appropriate pharmaceutical forms of administration are obtained.

With the acetylation of splenopentin, the object is attained of increasing the resistance to enzymatic degradation and thus of improving the bioavailability of the active ingredient.

BRIEF DESCRIPTION OF THE DRAWINGS

FIG. 3a1 is a multiple box and whisker plot of the number of plaque forming cells/spleen in mice exposed to FdTTP and treated with DAc-SP-5.

FIG. 3a2 is a multiple box and whisker plot of the number of plaque forming cells per 1 million spleen cells in mice exposed to FdTTP and treated with DAc-SP-5.

FIG. 3b1 is a multiple box and whisker plot of the number of plaque forming cells/spleen in mice exposed to FdTTP and treated with DAc-SP-5.

FIG. 3b2 is a multiple box and whisker plot of the number of plaque forming cells per 1 million spleen cells in mice exposed to FdTTP and treated with DAc-SP-5.

DETAILED DESCRIPTION OF PREFERRED EMBODIMENTS

To detect the immunological effects, the following models were used to begin with:
  the quantitative in vitro increase in T4 antigens on the surface of human T lymphocytes in patients with systemic lupus erythmatosus (SLE) (Example 8, Table 1) and
  the formation of antibodies against sheep erythrocytes (plaque-forming spleen cells) by AB/Bln. mice after X-ray irradiation (Example 8, Table 2).

The acylated splenopentins (Ac-SP5), produced pursuant to the invention, have other pharmacological properties, especially those for the normalization of the immune system. They are therefore also suitable for use for the following medical indications:

Treatment of viral infections (Example 13, Tables 3.1. to 3.3.)

Ac-SP5 have proven to be suitable drugs against influenza viruses or as drug for the treatment of pancreatitis after infection with coxsackieviruses. With regard to the extent of the stimulation of anti-viral immune defense, it has been noted that, on administration of virus amounts leading to an infection of moderate severity, the disease can be totally prevented, and that the virus dose required to initiate a disease of equal severity is ten times higher under treatment than in individuals without therapy.

Figure 1A:
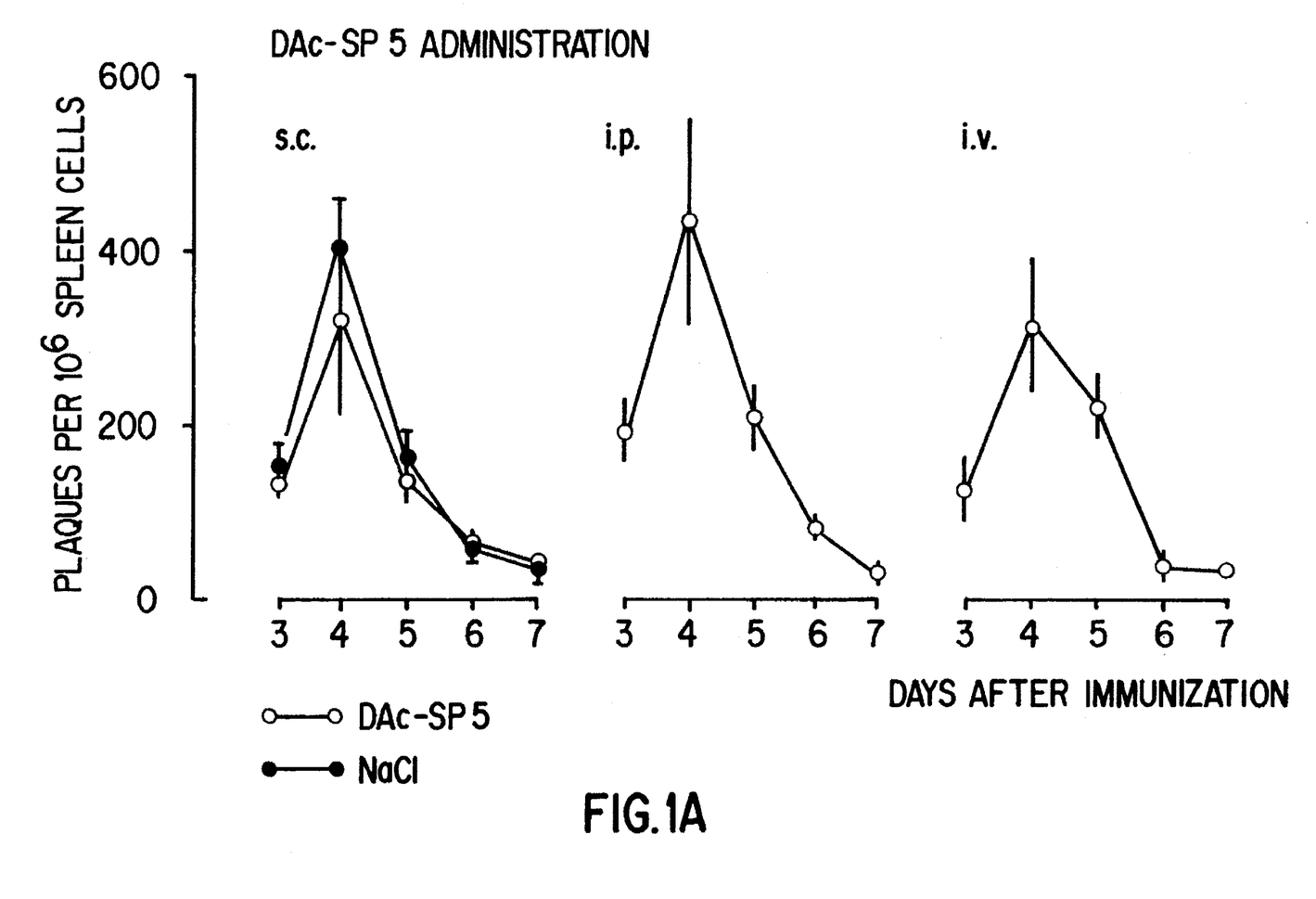
FIG. 1A is a graph of the number of plaques per $10^6$ spleen cells versus number of days of treatment with DAc-SP-5.
Figure 1B:
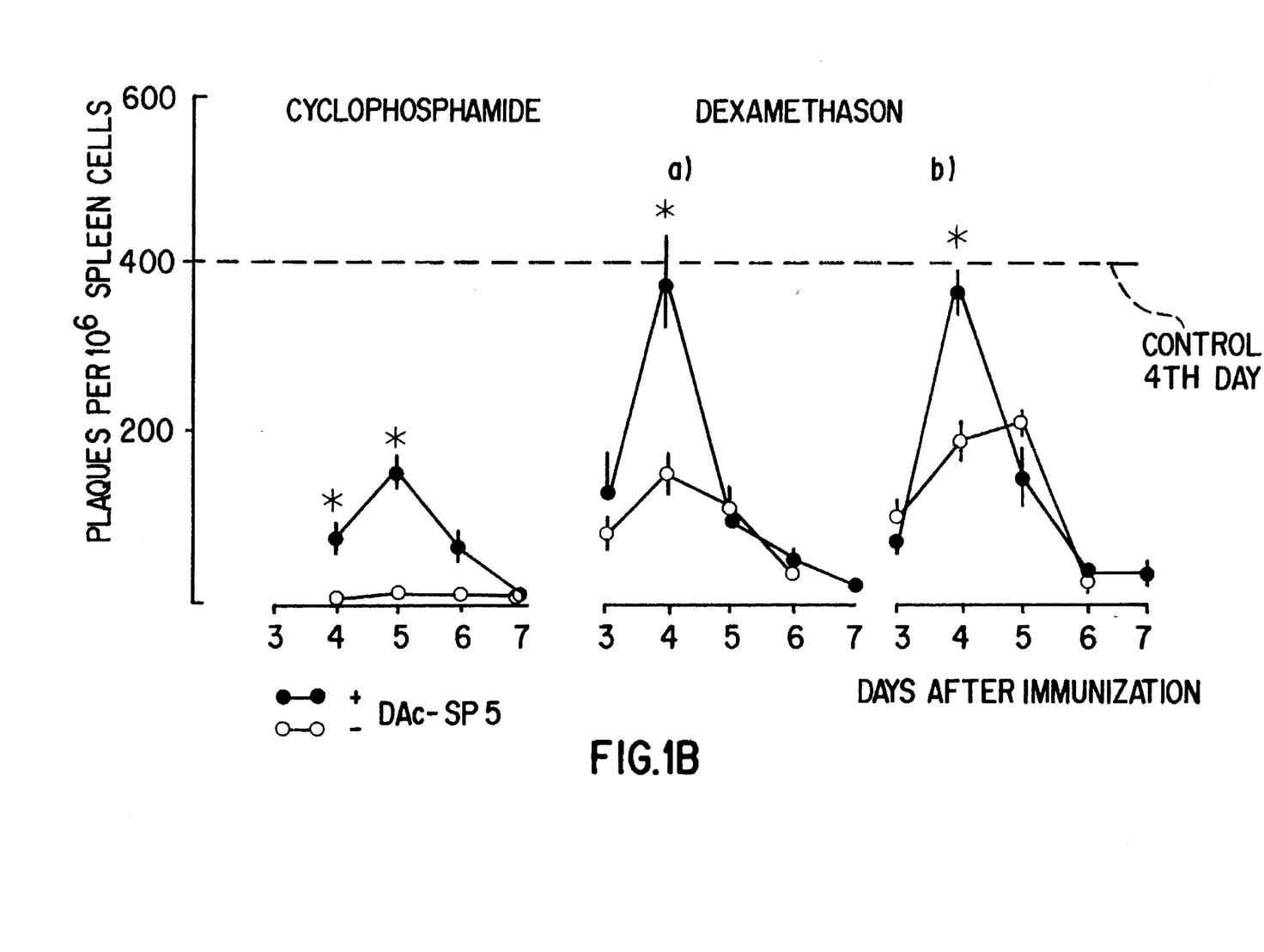
FIG. 1B is a graph of the number of plaques per $10^6$ spleen cells versus number of days of treatment with DAc-SP-5 after suppression of the immune system.

Treatment after chemotherapy (Example 14, FIG. 1, Table 4.1.)

The drugs are suitable for overcoming immonosuppressive states after chemotherapeutic measures, for example, for the treatment of cancer or as a result of overdoses of cyclosporin therapy.

The normalization of the humoral immunological response after cyclophosphamide or dexamethasone treatment of mice can be achieved by the administration of Ac-SP5. However, Ac-SP5 have no effect on the development of the normal antigen-specific humoral immunological response, so that disadvantageous immunomodulatory side effects are not to be expected (FIG. 1.).

Ac-SP5 brings about the accelerated reconstitution of the immunological system of patients with secondary immunological deficiency as a result of immunosuppressive therapy (Table 4.1.).

Figure 2:
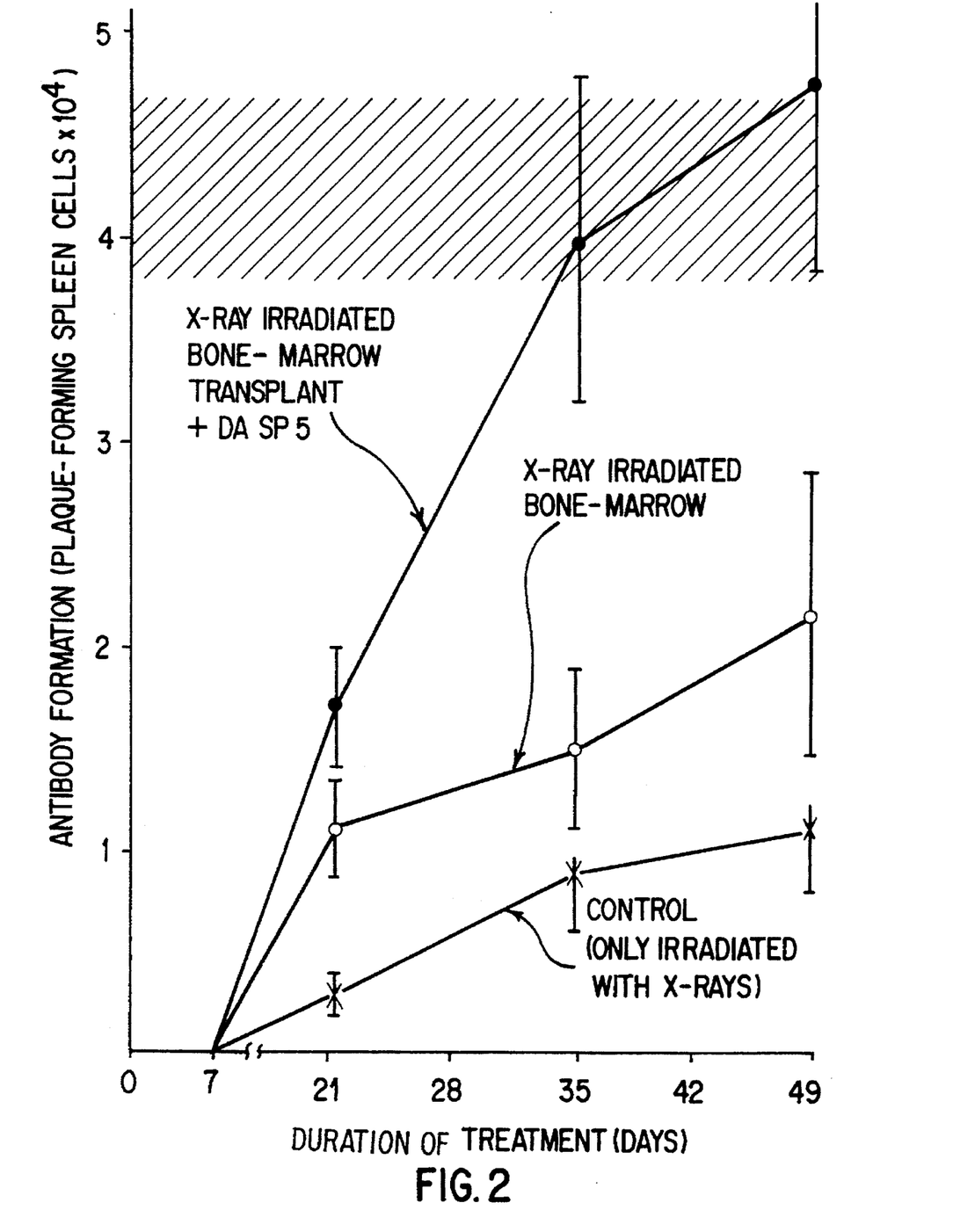
FIG. 2 is a graph of plaque forming spleen cells versus number of days of treatment with DAc-SP-5 after suppression of the immune system.

Stimulation of the growth and maturation of bone marrow cells (Example 15, Tables 5.1. to 5.2., FIG. 2)

The use of compounds, synthesized pursuant to the invention, leads to an in vitro increase in the rate of formation of stem cell colonies from mouse bone marrow cells, which were co-cultivated in agar with leukocytes of normal persons or SLE patients. The increased formation of "colonies" as a result of the presence of Ac-SP5 is an indication that the proliferation of immature stem cells of the bone marrow is stimulated directly by Ac-SP5 and/or that human leukocytes, under the influence of Ac-SP5, increasingly secrete colony-forming factors (Table 5.1.).

In mice, irradiated sublethally and with transplanted syngeneic bone marrow cells, an accelerated reconstitution of the humoral immune response is to be observed (FIG. 2).

With immunosuppressive or cytostatic therapy, the active ingredients can be used after irradiation and after bone marrow transplants. They are effective owing to the fact that they have specific binding sites (receptors) on human bone marrow cells (especially stem cells), which can be detected by radio-ligand binding studies. Such binding sites are also found on thymocytes and can be detected by $^3$H-labeled splenopentin or by $^{125}$iodine-labeled DAc-SP5 (Table 5.2.).

Treatment of HIV Infections (Example 16, Table 3 and FIG. 3)

In the case of HIV-infected patients, the administration of DAc-SP5 brings about an increase in the total lymphocyte count in the control area, as well as an increase in the absolute count of $CD3^+$, $CD4^+$ and $DR^+$ cells, as well as an improvement in the $CD4^+/CD8^+$ ratio. No side effects occurred after a 16-week treatment (Table 6.1.).

A combination with the cytostatic agent and revertase inhibitor azidothymidine, which is used in AIDS therapy, as well as with more effective substances of this type (fluorothymidine) leads to an accelerated normalization of the disadvantageous changes in the immunological system brought about by these substances (FIG. 3).

Prevention of Immunosuppressive Effects of Chronic Intoxications (Example 17, Table 7)

The effect of the Ac-SP5 consists therein that the suppression of the antigen-specific humoral immunological reaction, induced by alcohol and other chronically acting noxae, as well as the decrease in the number and activity of phagocytizing cells is canceled and the partial atrophy of the thymus and the spleen is prevented.

Therapy of Autoimmune reactions (Example 18, Tables 8.1. to 8.2.)

The substances, synthesized pursuant to the invention, are suitable for the treatment of various diseases with an autoimmune component (shown by the example of the induced autoimmune reaction against neuroantigens (Table 8.1.)), such as rheumatoid arthritis, SLE and atopic reactions. However, they do not bring about the disadvantageous reduction in the antigen-specific antibody titer after immunization has been effected (Table 8.2.).

EXAMPLES

1. Synthesis of Arginyl (N$^\epsilon$-acetyl-lysyl) glutamylvalyl-tyrosine (N$^\epsilon$-MAc-SP5)

1.1 Acylation

Boc-arg-lys-glu-val-tyr-OH × 2HOAc (1.83 g, 2 mmoles) is dissolved in 5 mL of dimethylformamide and reacted with 0.487 g (2.2 mmoles) acetyl-ONB. After 1 hour, the reaction mixture is added to N HCl and the precipitated product is filtered off with suction and washed with water until neutral. After reprecipitating from methanol/ethyl acetate, 1.72 g (96.3% of the theoretical yield) of boc-arg-lys(ac)-glu-val-tyr-OH × HOAc are obtained.

1.2 Splitting Off the Protective Groups

Boc-arg-lys(ac)-glu-val-tyr-OH × HOAc (1.34 g, 1.5 mmoles) is treated for 30 minutes with 10 mL trifluoroacetic acid/dichloroethane (1:1) and, after the excess trifluoroacetic acid is distilled off, precipitated from methanol with ether.

Yield: 1.34 g (92.8% of the theoretical)

arg-lys(ac)-glu-val-tyr-OH × 2 TFA

The corresponding N$^\epsilon$-Mac-SP5 × 2 HCl is obtained by lyophilization from dilute hydrochloric acid.

Molecular weight: 809.76; empirical formula: $C_{33}H_{56}N_9O_{10}Cl_2$

2. Synthesis of Arginyl-(N$^\epsilon$-palmitoyl-lysyl)-glutamylvalyltyrosine ($\epsilon$-pal-SP5)

2.1 Acylation

Boc-arg-lys-glu-val-tyr-OH × 2HOAc (1.83 g, 2 mmoles) is dissolved in 5 mL of DMF and reacted with 0.919 g (2.2 mmoles) of Pal-ONB. Working up and purification are carried out as in 1.1

Yield: 2.07 g (94.6% of the theoretical)

Boc-arg-lys(pal)-glu-val-tyr-OH × HOAc 2.2 Splitting Off the Protective Groups

Boc-arg-lys(pal)-glu-val-tyr-OH × HOAc (1.64 g, 1.5 mmoles) is treated for 30 minutes with 10 mL trifluoroacetic acid/dichloroethane (1:1) and, after the excess trifluoroacetic acid is distilled off, precipitated from methanol with ether.

Yield: 1.63 g (93.7% of the theoretical)

Arg-lys(pal)-glu-val-try-OH × 2 TFA

The corresponding $\epsilon$-pal-SP5 × 2 HCl is obtained by lyophilization from dilute hydrochloric.

Molecular weight: 1090.2; empirical formula: $C_{48}H_{92}N_9O_{14}Cl_2$

3. Synthesis of (N$^\alpha$-acetyl-arginyl)lysylglutamylvalyltyrosine ($\alpha$-MAc-SP5)

3.1 Acylation

Arg(NO$_2$)-lys(Z)-glu(OBzl)val-tyr-OBZM$_n$1 × TFA is dissolved in 5 mL of dimethylformamide and, after addition of 180 µL N-methylmorpholine (or a different tertiary amine) reacted with 0.265 g (1.2 mmoles) N-acetoxy-norborn-5-ene-2,3-dicarboximide.

After 30 minutes, the reaction mixture is added with stirring to N HCl and the precipitate is filtered off with suction and washed with water. The product is dissolved in about 10 mL dimethylformamide, precipitated with 5% NaHCO$_3$ solution, filtered and washed with water. After reprecipitation from methanol/ether, 1.05 g (96.2% of the theoretical) of protected N$^\alpha$-acetylsplenopentin are obtained,

3.2. Splitting Off the Protective Groups

The protected acetylpeptide is suspended in 90% acetic acid and hydrogenated in the presence of palladium black.

Yield: 760.8 g (95.6% of the theoretical) of N$^\alpha$-acetyl-SP5 × 2HOAc.

Molecular weight: 856.94; empirical formula: C$_{37}$H$_{62}$N$_9$O$_{14}$.

4. Synthesis of (N$^\alpha$-acetyl-arginyl)(N$^\epsilon$-acetyl-lysyl)glutamylvalyltyrosine (DAc-5SP5)

4.1. Synthesis of DAc-SP5 by Reacting SP5 with N-Acetoxy-norborn-5-ene-2,3-carboximide (II)

Arg-lys-glu-val-tyr-OH × 3HOAc (SP5) (43.7 g, 50 mmoles) is dissolved in 150 mL water and mixed with a solution of 33.2 g (150 mmoles) of acetyl-ONB in 100 mL dimethylformamide. Dimethylformamide is added, until a homogeneous solution is obtained. After stirring for one hour at room temperature (DC control) the solvent is removed under vacuum and the residue is triturated with ether or ethyl acetate. The solid material is filtered off, washed with ether and dried under vacuum over KOH.

Yield: 38.54 g (92% of the theoretical)

DAc-5PS x HOAc

The corresponding DAc-SP5 × HCl × 2H$_2$O is obtained by lyophilization from dilute hydrochloric acid.

Molecular weight: 850.39

Empirical formula: C$_{35}$H$_{60}$N$_9$O$_{13}$Cl calc. C 49.43 H 7.11 N 14.83 found 48.62 7.26 14.00

4.2. Synthesis of DAc-SP5 by Reaction of SP5 with 1-Acetoxybenzotriazole (Acetyl-OBt)(III)

The reaction of SP5 with acetyl OBt and the working up are carried out as in 4.1.

Yield: 90% of the theoretical.

Synthesis of (N$^\alpha$-Palmitoyl-arginyl)lysylglutamylvalyltyrosine ($\alpha$-pal-SP5)

5.1. Acylation

H-arg(NO$_2$)-lys(Z)-glu(OBzl)-val-lys-OBzl × TFA (1.16 g, 1 mmole) is dissolved in 5 mL dimethylformamide and, after addition of 120 µL of N-methylmorpholine (or a different tertiary amine), reacted with 0.626 g (1.2 mmoles) of (N-oxy-norborn-5-ene-2,3-dicarboximide) palmirate.

After working up as in 3.1 and precipitating from methanol/ether, 1.21 g (94.3% of the theoretical) of protected N$^\alpha$-palmitoylsplenopentin are obtained.

5.2. Splitting Off the Protective Groups

The protected palmitoylpeptide is suspended in 90% acetic acid and hydrogenated in the presence of palladium black.

Yield: 920 mg (92.7% of the theoretical) of N$^\alpha$-pal-SP5 × 2 HOAc

Molecular weight: 1035.29; empirical formula: C$_{51}$H$_{88}$O$_{13}$N$_9$

6. Synthesis of N-Acetoxy-norborn-5-ene-2,3-dicarboximide (Acetyl-ONB)

N-Hydroxy-norborn-5-ene-2,3-dicarboximide (17.92 g, 0.1 mole) is largely dissolved in 100 mL chloroform and 21 mL (0.15 moles) triethylamine, followed by adding 19 mL (0.2 moles) acetic anhydride at 0° C. with stirring. After stirring for 2 hours at room temperature, the solvent is largely removed, the residue is mixed with water and the precipitate is filtered off.

After recrystallization from isopropanol/water, 19.33 g (87.4% of the theoretical) of acetyl-ONB are obtained.

Melting point: 112.5°–113.5° C.

7. Synthesis of 1-Acetoxy-benzotrtazole (acetyl-OBt)

1-Hydroxybenzotriazole (13.51 g, 0.01 moles) is dissolved in 100 mL chloroform. After addition of 16.8 mL (0.12 moles) triethylamine, the solution is cooled to 0° C. and 19 mL (0.2 moles) of acetic anhydride are added with stirring. Stirring is then continued for 2 hours at room temperature. The solid, remaining after the solvent is removed, is recrystallized from ethyl acetate or benzene.

Yield: 14.88 g (84% of the theoretical)

Melting point: 96°–98° C.

8. Immunobiological Effect of $\epsilon$-MAc-SP5

$\epsilon$-MAc-Sp 5 (sequence 32 to 36 of the spleen hormone splenin) has the same or similar immunobiological effects as the total splenin molecule. For example, $\epsilon$-MAc-SP 5 induces the quantitative increase of T4 antigens on the surface of T-lymphocytes, which are detectable on the surface of normally functioning T helper lymphocytes. Normally functioning T helper lymphocytes stimulate antibody formation. To detect an increase in antibody formation due to $\epsilon$-MAc-SP 5, a relevant animal model experiment was selected: AB/Bln. mice were irradiated sublethally with X-rays and then treated with or without $\epsilon$-MacSP 5. At the same time, the animals were immunized with sheep erythrocytes. Since sublethally irradiated animals lose the ability to produce quantitatively sufficient antibodies, an increased formation of antibodies to sheep erythrocytes in $\epsilon$-MAc-SP 5 treated animals is a measure of the regeneration of the immunological system by $\epsilon$MAc-SP 5. After 34 days, animals treated with $\epsilon$-MAc-SP 5 were already able to form antibodies in the same amount as unirradiated control animals. By comparison, animals not treated with $\epsilon$-MAc-SP5 were able to do so only 48 days after a single irradiation with X-rays. The invention will be explained in greater detail by means of examples of the operation (Tables 1 and 2).

Testing

8.1. Increase in T4 Antigens on the Surface of Human Lymphocytes After Contact With $\epsilon$-MAc-SP 5

Normally functioning (mature) T helper lymphocytes have T4 antigens, T suppresser lymphocytes and T8 antigens on their surface. In patients with systemic lupus erythmatosus (SLE), the T4 antigen content on the lymphocyte surface was determined to be reduced by means of monoclonal antibodies. As a consequence of therapeutic measures, the values normalized. If the lymphocytes of the patients were brought into contact with $\epsilon$-MAc-SP5 before the treatment, an individually different, yet permanently increased number of T4 antigens were detectable (Table 1) after a 2-hour incubation. The T8 antigens (surface antigens on T suppresser lymphocytes), or cytotoxid T lymphocytes, on the other hand, did not change quantitatively. T4 antigens increase, if the T4 cells increase or if the antigens are expressed increasingly on their surface. The investigations revealed that the lymphocytes of the SLE patients did not incorporate 3H-thymidine at an increased rate after contact with ε-MAc-SP5 (910±180 pulses per minute without ε-MAc-SP-5 contact; 820±210 pulses per minute after contact with ε-MAc-SP5; n: 5, no significant deviation in the t test). We therefore assume that the increase in T4 antigens did not come about due to an increase in the T4 antigens, but rather is the result of a structural change in the T cell surface, which is possibly identical with a "maturing process" of the cell. Mature, normally functioning T helper lymphocytes stimulate antibody formation through B lymphocytes. It was therefore investigated whether the formation of antibodies against defined antigens (sheep erythrocytes) is increased after systemic ε-MAc-SP-5 application.

8.2. Antibody Formation After Immunological Suppression and Systemic ε-MAc-SP5 Medication A relevant animal model experiment was used to demonstrate the effect on antibody formation. Four-month old AB/Bln. Mice (Akademie der Wissenschaften der DDR (Academy of the Sciences of the DDR), Berlin Book) were treated systemically (sublethally) with X-rays (600 c Gy) and treated subsequently with or without ε-MAc-Sp 5 (Animal Groups Nos. 1, 2 and 3 of Table 2). A further group of animals was neither irradiated with X-rays nor treated with ε-MAc-SP 5 (Group No. 4, Table 2). Animal groups Nos. 2 and 3 were treated on the next day either with 10 μg or 50 μg ε-MAc-SP 5 (intraperitoneal application). At different intervals of time after the irradiation (14th day, 20th day, etc. Table 2), the extent of the formation per animal of antibodies against sheep erythrocytes was determined by means of the JERNE plaque test (as modified by Eckert et al. (Eckert, R., Pfuller, U., Kindt, A., Reichelt, E. and Franz, H.): Histamine receptor-carrying lymphocytes. III. Suppression of immunological reactions after killing the histamine receptor-carrying lymphocytes by a conjugate of histamine and the A-chain of mistellectin I. Biomed. Biochim. Acta 44 (1985) 1239–1246.). For this purpose, the animals were immunized 5 days before the investigation with sheep erythrocytes (intraperitoneal application of $5\times10^8$ cells per animal) and examined on the day given in Table 2 with respect to their ability to form antibodies against sheep erythrocytes (for details of the method see Diezel, W. et al., Biomed, Biochim Acta 45 (1986) 1349 to 1352).

It is well known that animals, irradiated sublethally, lose their ability to form sufficient antibodies. Normal formation occurs only after a certain latent period, during which the antibody-forming cells of the animals are regenerated. In our experiments, the animals were able to form antibodies in the same amount as the unirradiated control animals no earlier than 48 days after the single irradiation with X-rays (no significant difference between Nos. 1 and 4 on day 48, Table 2). In comparison with this, animals treated with ε-MAc-SP5 were capable of producing antibodies normally already on the 34th day after irradiation with X-rays (no significant difference between the No. 2 and No 4 values or the No. 3 and No. 4 values on day 34, Table 2).

The results presented justify the assumption that ε-MAc-SP5 can have a favorable effect on weaknesses in the immunological defense. Such a condition is inherited or acquired. An acquired weakness in the immunological defense can arise as a consequence of necessary therapeutic measures (treatment with cytostatic agents or irradiation in the case of cancer affections) or is inevitable in the case of AIDS in the later stages of the disease. According to the results presented, it should be possible to eliminate with ε-MAc-SP5 at least partially such an impaired function of the immunological system.

TABLE 1

Quantitative increase in T4 antigens on the surface of human T lymphocytes after contact with ε-MAc-SP5. Determination of the T4 antigen by means of monoclonal antibodies (VIT4-CD4 clusters and VIT8-CD8 clusters). T lymphocytes of patients with systemic lupus erythmatosus (SLE).

| Patient No. | (SLE) | | T Cell Surface Antigens (%) | |
|---|---|---|---|---|
| | | | T4 | T8 |
| 1. | Schr., R. | Control (C) (without ε-MAc-SP5) | 1 | 10 |
| | | +ε-MAc-SP5 | 54 | 10 |
| 2. | H., A. | C | 48 | 40 |
| | | +ε-MAc-SP5 | 60 | 48 |
| 3. | J., Ra | C | 44 | 50 |
| | | +ε-MAc-SP5 | 66 | 48 |
| 4. | O., H. | C | 42 | 12 |
| | | +ε-MAc-SP5 | 65 | 15 |
| 5. | W., B. | C | 45 | 40 |
| | | +ε-MAc-SP5 | 67 | 42 |

TABLE 2

Formation of antibodies against sheep erythrocytes (plaque-forming spleen cells) by AB/Bln. mice after a single X-ray irradiation of the animals with 600 c Gy and subsequent treatment with ε-MAc-SP5. Peptide application of 10 μg and 20 μg per animal on subsequent day. Each value (average value ± scatter) represents the average value of at least 5 animals.

| | | Number of Plaque-Forming Spleen Cells per Spleen | | | | | |
|---|---|---|---|---|---|---|---|
| No. | Treatment | Day 14 | Day 20 | Day 27 | Day 34 | Day 41 | Day 48 |
| 1. | X-ray irradiation | 1600 ± 600 | 1500 ± 500 | 4000 ± 1000 | 1200 ± 2500 | 28000 ± 7800 | 40000 ± 6600 |
| 2. | X-ray irradiation* + MAc-SP 5 (10 μg) | 3200 ± 1500 | 4400 ± 1000 | 17000 ± 2000 | 41000 ± 9500 | 44000 ± 8500 | 44500 ± 4000 |
| 3. | X-ray irradiation + MAc-SP 5 (50 μg) | 3000 ± 400 | 5200 ± 900 | 15000 ± 3000 | 39000 ± 7000 | n.d.** | n.d. |
| 4. | no X-ray irradiation no MAc-SP 5 | 44100 ± 6600 | 42500 ± 4000 | 44000 ± 5500 | 44000 ± 8000 | 43000 ± 9300 | 43500 ± 9000 |

*U test (Mann and Whitney). Comparison between Nos. 1/2 and 1/3: Day 14: p 0.05; Day 20 P 0.001; Day 34: p 0.001; comparison Nos. 1/2,: Day 41: p 0.01; Day 48: no significant difference. Comparison 2/4 and 3/4: day 34: no significant difference.
**n.d. = not determined.

EXAMPLE 9

Separation of Mono-, Di- and Triacetylsplenopentins (Mono-, Di- and Triacetyl-SP5), Monoacetyl ($N^\alpha$-Arg)-SP-5; Diacetyl($N^\alpha$-Arg, $N^\epsilon$-Lys)-SP-5; Triacetyl($N^\alpha$-Arg, $N^\epsilon$-Lys-O-Tyr)-SP5

On a column 150 mm long and 9 mm in diameter (V=9.54 mL), which contains a carboxylated cation exchanger with a particle size of 50–90μ, 50 mg of an equimolar mixture of mono-, di- and triacetyl-SP5 are applied.

The substances are eluted at a flow rate of 5 mL/hour with 11.5% ethanol having a pH of 2.45 (acetic acid). The substances are eluted in the sequence monoacetyl, diacetyl and triacetyl-SP5 with R>1 and with a recovery rate of better than 95%.

EXAMPLE 10

Separation of Monoacetyl ($N^\alpha$-Arg)-SP5 and Monoacetyl($N^\epsilon$-Lys)-SP5

On a column 200 mm long and 9 mm in diameter (V=12.7 mL), which contains as support material a carboxylated cation exchanger with a particle size of 40 to 50μ, an equimolar mixture of monoacetyl($N^\alpha$-arg)-SP5 and and monoacetyl($N^\epsilon$-lys)-SP5 is applied. The elution takes place with an aqueous solvent having a pH of 2.35 (HCl) at a flow rate of 10 mL/hour. The substances are eluted in accordance with their polarity (1st monoacetyl-($N^\alpha$-arg)-SP5; 2nd monoacetyl ($N^\epsilon$-lys)-SP5) with a recovery rate of 97% The resolution is 1.5.

EXAMPLE 11

Separation of Triacetyl($N^\alpha$-Arg, $N^\gamma$-Arg, $N^\epsilon$-Lys)-SP5 and Diacetyl($N^\alpha$-Arg, $N^\epsilon$-Lys)-SP5

On a column 200 mm long and 5 mm in diameter, which contains a carboxylated cation exchanger with a particle size of 50 to 60μ as support, a mixture of 5 mg of each of the two peptides is applied. The elution is carried out at a flow rate of 3 mL/hour with 11.5% ethanol with a pH of 2.57 (acetic acid). A resolution of 0.8 with a recovery rate of 96% per substance is achieved.

EXAMPLE 12

Separation of a Crude Synthesis Product of Acylated Splenopentins

Substances contained:
1. Monoacetyl($N^\alpha$-arg)-SP5
2. Diacetyl($N^\alpha$-arg, $N^\epsilon$-lys)-SP5 (main product, constituting 75% according to HPLC)
3. Triacetyl($N^\alpha$arg, $N^\gamma$-arg, $N^\epsilon$-lys)-SP5
4. Triacetyl($N^\alpha$-arg, $N^\epsilon$-lys-O-tyr)-SP5
5. Diacetyl($N^\alpha$-arg, $N^\epsilon$-lys, D-tyr)-SP5

On a column, 60 cm long and 10 cm in diameter, which contains 4.5 L of a carboxylated cationic exchange resin with a particle size of 50 to 90μ, 35 g of a splenopentin synthesis product in 150 mL elution solution are applied. The mixture of substances is separated by isocratic elution with 10% ethanol having a pH of 2.5 (acetic acid) at a flow rate of 80 mL/min. The fractionated eluate is measured at 276 mm. Subsequently, the peak volumes are combined, the resultant solution is evaporated to dryness and the residue lyophilized with addition of equimolar amounts of hydrochloric acid.

Total recovery rate: 95.6%
Main product: 19 g (54.3%)
HPLC of main product: 98.5% pure.

EXAMPLE 13

Treatment of Viral Infections

TABLE 3.1

Effect of the DAc-SP5 treatment on the mortality of Balb/c mice after infection (intranasally) with the influenza virus A/PR/8/34 (n = 10 – 12)

| Infection Dose ($EID_{50}$) | $10^1$ | $10^2$ | $10^3$ | $10^4$ | $10^5$ |
|---|---|---|---|---|---|
| Mortality rate after 6 days in % | (a) | (b) | (c) | | |
| Control | 50 | 66.6 | 100 | 100 | 100 |
| DAc-SP5 Treatment during the Infection* | 33.3 | 33.3 | 66.6 | 100 | 100 |
| DAc-SP-5 before the Infection** | n.t. | n.t. | n.t. | 100 | 100 |

(a) n.s.
(b) $p < 0.05$
(c) $p < 0.01$
(t-test)

TABLE 3.2

Effect of DAc-SP5 treatment on the development of a histologically confirmed pancreatitis after infection with the coxsackievirus B4 (Balb/c mice) (n = 10 – 25)

| | Infection Dose ($TCID_{50}$) | | | |
|---|---|---|---|---|
| Animals with Pancreatitis (in %, n = 10 – 25) | $10^3$ (a) | $10^4$ (b) | $10^5$ | $10^6$ |
| Control | 60 | 60 | 100 | 100 |
| DAc-SP5 Treatment During the Infection* | 0 | 0 | 60 | 100 |
| DAc-SP5 Treatment Before the Treatment** | n.t. | 80 | 100 | 100 |

TABLE 3.3

Effect of DAc-SP5 treatment on the development of histopathological changes in the lung of the mouse (Balb/c) and the Syrian hamster (n = 9 – 10)

| | Number of Animals with Histopathological Lung Findings (%) | | |
|---|---|---|---|
| | Control | DAc-SP5 Therapy* During the Infection | DAc-SP5 Therapy** Before the Infection |
| Hamster ($TCID_{50}$ = $2 \times 10^{3.5}$) | 100 | 10 | 100 |
| Mouse (TCID = $10^{3.5}$) | 100 | 0 | 100 |

*0.5 mg DAc-SP5. s.c. (per kg), administered daily over 5 days, treatment started on the day of the infection
**0.5 mg DAc-SP-5 per kg, s.c., 3 times per week for two weeks before the start of the infection
n.t. = not tested

EXMPLE 14

Treatment After Chemotherapy

FIGS. 1A and 1B

Effect of DAc-SP-5 and Immunosuppressive Compounds on the Antigen-Specific IgM Response in Mice

A

Independently of the nature of the application, the administration of the therapeutic dose of DAc-SP5 (3 times, at intervals of 24 hours, 0.5 mg/kg) has no significant effect on the strength and kinetics of the IgM response of mice to sheep erythrocytes.

Animals: male NMRI mice (colony bred) aged 2 to 2.5 months.

Method corresponding to the Jerne Plaque Test: R. Eckert and G. Pasternak, Acta biol. med. germ. 31:127–137 (1973)

n = 16 (NaCl control), n = 8 (4DAc-=SP5 (DAc-trials)

B

After a few consecutive applications, DAc-SP5 has already reconstituted the chemical induced suppression of the humoral immunological response, The almost complete suppression of the antigen-specific IgM response, initiated by a single administration of cyclophosphamide (7.2 mg/animal, i.p.) is partially reconstituted by treatment with DAc-SP5 (0.5 mg/kg, s.c.) on the four subsequent days.

The reduction of the antigen-specific IgM response by the administration of dexamethasone(a) = 0.2 mg/animal, i.p.; b) = 0.08 mg/animal, i.p.) is reconstituted completely by DAc-SP5 (0.5 mg/kg, s.c.) administration on the two subsequent days.

*=p 0.05 (comparison with the corresponding value without DAc-SP5 treatment)

n = 6–8 experimental animals as with A.

TABLE 4.1

Cytofluorimetric detection (quantitative determination) of monocyte or lymphocyte subpopulations by means of monoclonal antibodies in a female patient with secondary immunological deficiency before and while receiving diacetyl splenopentin medication, the therapy otherwise remaining unchanged.

| Parameter | Normal Values | Before Treatment | Therapy with Dac-SP5 2 (Weeks) | 3 | 4 |
|---|---|---|---|---|---|
| Lymphocytes (Gpt/L) | 1.5–3.5 | 0.28 | 0.84 | 0.74 | 0.83 |
| CD 3 (Gpt/L) | 1.0–2.0 | 0.04 | 0.39 | 0.55 | 0.67 |
| CD 4 (Gpt/L) | 0.6–1.3 | 0.03 | 0.29 | 0.34 | 0.38 |
| CD 4/CD 8 | 1.5–3.0 | 0.58 | 2.3 | 2.2 | 2.4 |
| DR+-monocytes (Gpt/L) | 0–0.6 | 0.02 | 0.08 | 0.26 | 0.60 |
| DR+-monocytes (%) | 65–90 | 16 | 22 | 62 | 72 |

EXAMPLE 15

Stimulating the Growth and Maturation of Bone Marrow Stem Cells

TABLE 5.1

Number of cell "colonies" after cultivating bone marrow stem cells of C57 Bl mice and leukocytes of control persons or of patients with systemic lupus erythematosus in the presence of different DAc-SP5 concentrations (colony-forming test). All numerical values represent the percentage averages of 4 parallel cultures, based on the "colonies" without addition of DAc-SP5 (Method: Schunck, H. et al. (1987): Biomed. Biochim. Acta 46:581).

Cell "colonies" per $10^5$ bone marrow cells without and after cultivating the cells with DAc-SP5. Percentages are based on the "colonies" that have not been cultivated with DAc-SP5 (=100%). DAc-SP5 concentration per 1 mL of semisolid agar.

| Group | Exp. | 1 µg | 2 µg | 10 µg | 20 µg |
|---|---|---|---|---|---|
| Control persons | A | 99 | 98 | 114 | 125 |
|  | B | 135 | 136 | 147 | 187 |
| Patients (systemic lupus erythematosus) | A | 180 | 316 | 270 | 256 |
|  | B | 284 | 873 | 642 | 430 |

TABLE 5.2

Detection of the binding site for $^3$H-splenopentin and $^{125}$I-diacetyl splenopentin, displaceable by the unlabeled ligand, by means of radioligand bonding studies* and affinity calculation by means of computer-aided affinity spectrum analysis**

| Cell Type/Species | Radioligand Dissociation Constant $(K_D, M)$*** $^3$H-SP5 (n = 2 – 5) | $^{125}$I-DAc-SP5 (n = 2 – 4) |
|---|---|---|
| Bone Marrow/Rat | $8.7 \pm 2.2 \times 10^{-8}$ | $8.5 \pm 0.5 \times 10^{-9}$ |
| Bone Marrow/Man | n.t. | $1.2 \pm 0.3 \times 10^{-8}$ |
| Stem Cell Line K 564/Man | $12 \times 10^{-8}$ | n.t. |
| Thymus Cells/Rat | $7.6 \pm 3.5 \times 10^{-8}$ | n.t. |
| Spleen Cells/Rat | no displaceable bond | n.t. |
| Peritoneal Mast Cells****/Rat | $4.3 \pm 1.3 \times 10^{-8}$ | n.t. |

*Method corresponding to that of H. Rapke and C. Liebmann, Membrane receptors and their effector systems, Academie Verlag, Berlin and VCH Weinheim, BRD (1982) pp. 55–101
**Method corresponding to that of H. Repke, Biochim. Biophys. Acta 929: 47–61 (1987)
***Calculated from values below the saturation range
****Cell preparation method of H. Repke el al., Agents and Actions, 20: 216–218 (1987)
n.t. = not tested FIG. 2 shows formation of antibodies against sheep erythrocytes (plaque-forming spleen cells by AB/Bln. mice) after a single X-ray irradiation of the animals with 800 oGy, followed by transplantation of syngeneic bone marrow cells and subsequent medication with 10 µg DAc-SP5 three times weekly (•) or without DAc-SP5 treatment (o). Each value (average ± scatter) represents the average of at least 5 animals. Hatched area: plaque-forming spleen cells of the animals without X-ray irradiation and without DAc-SP5 treatment. Minimum and maximum values within the experimental period of 49 days. Immunization of the animals with sheep erythrocytes 5 days before the determination of the IgM plaque-forming spleen cells.

EXAMPLE 16

Treatment of HIV Infections

FIGS. 3a1, 3a2, 3b1 and 3b2

The influence of diacetyl splenopentin on the effect of the HIV revertase inhibitor 3'-fluorothymidine-5'triphosphate (FdTTP) on the humoral immune reaction (E. Matthes et al. Biochem. Biophys, Res, Com. 148, 1, 1987, pages 78–85).

Figure 3A:
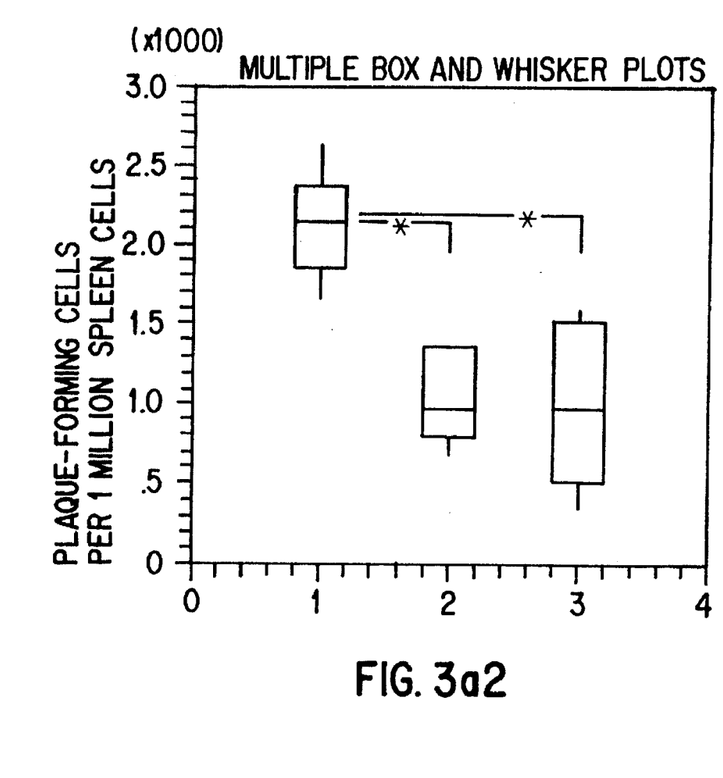
Figure 3A:
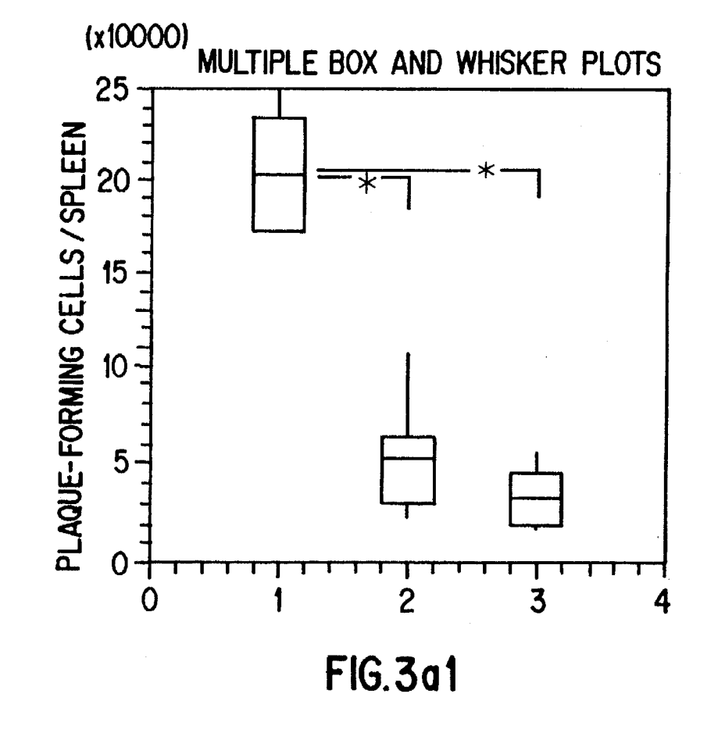

FIG. 3a1 and 2

A dose of 1 mg FdTTP was administered daily over 4 days by way of the drinking water to 2½-month old male Balb/c mice. Twentyfour hours after the substance was discontinued, DAc-SP5 was administered three times (0.5 mg/kg, s.c.) at 12-hour intervals. Twelve hours after the last DAc-SP5 treatment, the mice were immunized with sheep erythrocytes (i.p.). After a further 24 hours, the administration of FdTTP (s.o.) was renewed until the animals were killed (plaque test: 4th day after immunization).

| Group 1: | NaCl control | (n = 6) |
|---|---|---|
| Group 2: | FdTTP | (n = 6) |
| Group 3: | FdTTP + DAc-SP5 | (n = 6) |

Figure 3B:
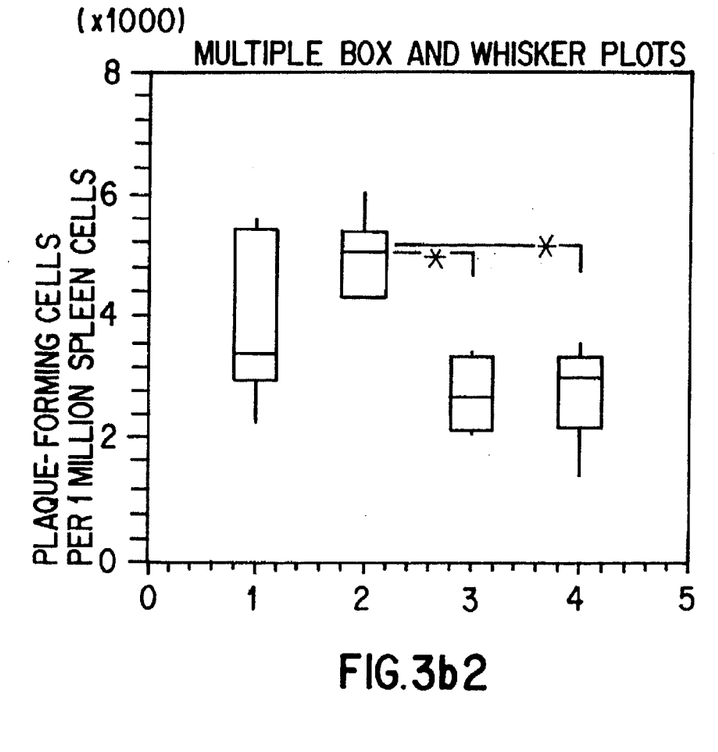
Figure 3B:
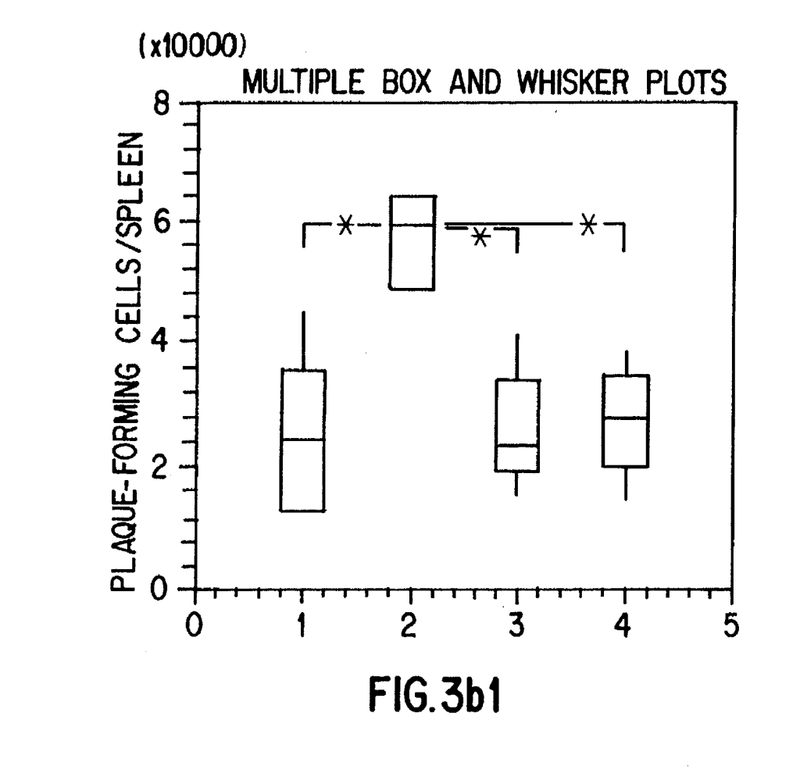

FIG. 3b1 and 2

Animals, method and substances as in 6.1.a

Duration of the FdTTP treatment: 11 days

Twentyfour hours after the FdTTP was discontinued, the administration of DAc-SP5 was continued at intervals of 24 hours over 5 days.

| Group 1: | DAc-SP5 control | (n = 6) |
|---|---|---|
| Group 2: | FdTTP | (n = 6) |
| Group 3: | FdTTP + DAc-SP5 | (n = 6) |
| Group 4: | NaCl control | (n = 4) |

The box and whisker plot represents the data of a random sample by four regions of equal frequency. The box contains the average 50% of the random sample, the division is the median (if the distribution of the data is normal, the division is in the center of the box). The lines above and below the box sweep over the rest of the random sample.

\* = $p<0.05$

TABLE 6.1.a

Cytofluorometric detection (quantitative determination) of monocyte or lymphocyte subpopulations by means of monoclonal antibodies in HIV infected patients before and during therapy with diacetyl splenopentin

| Patient (Disease Stage) | Parameter | Normal Values | Before Treatment | Therapy with Splenopentin (Weeks) | | | | |
|---|---|---|---|---|---|---|---|---|
| | | | | 4 | 8 | 12 | 16 | 24 |
| No. 1 (G.Th.) | Lymphocytes (Gpt/L) | 1.5–3.5 | 1.44 | 2.85* | 2.88* | 1.88* | 2.02* | 1.53** |
| CDC: IIIb | CD 3 (Gpt/L) | 1.0–2.0 | 0.04 | 0.57 | 0.55 | 0.75 | 1.64* | 0.80 |
| | CD 4 (Gpt/L) | 0.6–1.3 | 0.10 | 0.17 | 0.17 | 0.28 | 1.01* | 0.29 |
| | CD 4/CD 8 | 1.5–3.0 | 0.21 | 0.32 | 0.26 | 0.58 | 1.85* | 1.50* |
| | $DR^+$-monocytes (Gpt/L) | 0–0.6 | 0.10 | n.d. | 0.28 | n.d. | 0.26 | 0.37 |
| | $DR^+$-monocytes (%) | 65–90 | 29 | n.d. | 65* | n.d. | 44 | 74* |
| No. 2 (S.H.) | Lymphocytes (Gpt/L) | 1.5–3.5 | 1.12 | 1.86* | 2.12* | 1.34 | 1.24 | |
| CDC: IVb | CD 3 (Gpt/L) | 1.0–2.0 | 0.01 | 0.02 | 0.53 | 0.43 | 0.71 | |
| | CD 4 (Gpt/L) | 0.6–1.3 | 0.06 | 0.13 | 0.15 | 0.11 | 0.17 | |
| | CD 4/CD 8 | 1.5–3.0 | 0.18 | 0.20 | 0.22 | 0.22 | 0.24 | |
| | $DR^+$-monocytes (Gpt/L) | 0–0.6 | 0.08 | 0.16 | n.d. | 0.20 | 0.32 | |
| | $DR^+$-monocytes (%) | 65–90 | 38 | 30 | n.d. | 40 | 37 | |

*The values marked with (*) correspond to normal values
n.d. = not determined

TABLE 6.1.b

Cytofluorometric detection (quantitative determination) of monocytes or lymphocytes populations by means of monoclonal antibodies in HIV infected patients before and during therapy with diacetyl splenopentin

| Patient (Disease Stage) | Parameter | Normal Values | Before Treatment | Therapy with Splenopentin (Weeks) | | | | |
|---|---|---|---|---|---|---|---|---|
| | | | | 4 | 8 | 12 | 16 | 24 |
| No. 3 (B.A.) | Lymphocytes (Gpt/L) | 1.5–3.5 | 1.3 | 3.30* | 3.81* | 2.58* | 1.84** | |
| CDC: IIIb | CD 3 (Gpt/L) | 1.0–2.0 | 0.05 | 0.53 | 1.18* | 1.78* | 1.20* | |
| | CD 4 (Gpt/L) | 0.6–1.3 | 0.02 | n.d. | 0.34 | 0.30 | 0.93 | |
| | CD 4/CD 8 | 1.5–3.0 | 0.05 | n.d. | 0.21 | 0.27 | 0.72 | |
| | $DR^+$-monocytes (Gpt/L) | 0–0.6 | 0.03 | 0.13 | n.d. | 0.24 | 0.41 | |
| | $DR^+$-monocytes (%) | 65–90 | 5 | 32 | n.d. | 54 | 67* | |

TABLE 6.1.b-continued

Cytofluorometric detection (quantitative determination) of monocytes or lymphocytes populations by means of monoclonal antibodies in HIV infected patients before and during therapy with diacetyl splenopentin

| Patient (Disease Stage) | Parameter | Normal Values | Before Treatment | Therapy with Splenopentin (Weeks) 4 | 8 | 12 | 16 | 24 |
|---|---|---|---|---|---|---|---|---|
| No. 4 (S.F) CDC: IIb | Lymphocytes (Gpt/L) | 1.5–3.5 | 1.30 | 2.02* | 1.07 | n.d. | 2.24* | |
| | CD 3 (Gpt/L) | 1.0–2.0 | 0.26 | 0.68 | 0.75 | n.d. | 0.74 | |
| | CD 4 (Gpt/L) | 0.6–1.3 | 0.08 | 0.04 | 0.47 | n.d. | 0.81* | |
| | CD 4/CD 8 | 1.5–3.0 | 0.06 | 0.20 | 0.27 | n.d. | 1.10* | |
| | DR$^+$-monocytes (Gpt/L) | 0–0.6 | 0.11 | 0.23 | 0.22 | n.d. | 0.45 | |
| | DR$^+$-monocytes (%) | 65–90 | 18 | 52 | 53 | n.d. | 72* | |

*The values marked with (*) correspond to normal values
n.d. = not determined

EXAMPLE 17

Prevention of Immunosuppressive Effects of Chronic Intoxications

TABLE 7

Effect of chronic alcohol intoxications on selected parameters of the immunological system of male Balb/c mice

| Administration of 15% ethanol over 1.5 months | + | + | – | – |
|---|---|---|---|---|
| 0.1 mg DAc-SP5 i.p., 5 times daily before test | – (n = 40) | + (n = 40) | + (n = 40) | – (n = 40) |
| % phagocytizing peritoneal cells | 29.0 ± 1.7 | 47.5 ± 1.7 | 75.0 ± 2.6 | 46.0 ± 1.7 |
| Phagocytosis index | 3.0 ± 0.08 | 4.5 ± 0.1 | 4.9 ± 0.15 | 3.7 ± 0.08 |

TABLE 7-continued

Effect of chronic alcohol intoxications on selected parameters of the immunological system of male Balb/c mice

| Thymus Mass (mg) | 15.0 ± 2.6 | 29.0 ± 2.2 | 40.0 ± 3.0 | 25.0 ± 2.3 |
|---|---|---|---|---|
| Spleen Mass (mg) | 60.0 ± 3.2 | 82.0 ± 5.6 | 95.0 ± 7.1 | 85.0 ± 3.6 |
| Plaque-forming cells of the spleen per $10^6$ cells (Jerne Plaque Test) | 61.3 ± 3.8 | 214.3 ± 5.9 | 285.0 ± 11.3 | 156.6 ± 12.0 |

Average values ± S.D

EXAMPLE 18

Therapy of Autoimmunological Reactions

TABLE 8.1

Normalizing effect of DAc-SP5 on the induced autoimmunological reaction to neuronal antigens in rabbits

| Experimental Groups[1] | % Antigen-specific reaction of basophils with neuro-antigen (rabbit) standard preparation | | | |
|---|---|---|---|---|
| | Initial Values | After 2 Weeks | After 6 Weeks | After 8 Weeks |
| 1. Hippocampus lesion[2] + DAc-SP5[3] n[4] = 6 | 31.3 ± 1.9 | 42.0 ± 4.8 | 28.3 ± 3.9 * | 15.0 ± 2.9 * |
| 2. Hippocampus lesion + NaCl n = 6 | 28.0 ± 4.0 | 44.0 ± 6.7 | 46.6 ± 7.0 | 38.6 ± 0.7 |
| 3. Control + DAc-SP5 n = 4 | 21.0 ± 5.0 | 20.5 ± 3.3 | 10.0 ± 2.7 | 23.0 ± 6.2 |
| 4. Control + NaCl n = 4 | 11.0 ± 3.0 | 20.5 ± 4.6 | 33.5 ± 3.3 | 22.5 ± 3.8 |

[1] Chinchilla rabbits (about 3,000 g) with spontaneous autoimmunological reaction to neuronal antigens.
[2] Local lesion of the dorsal hippocampus leads to an increase in the autoimmunological reaction to neuronal antigens.
[3] Administration of DAc-SP5 (1 mg/kg) 5 times at intervals of 4 days. * = p < 0.005 (student t test)
[4] n = number of animals

TABLE 8.2

Effect of DAc-SP5 on the titer of (antiovalbumin) antibodies[1]

| | log$_2$ PCA Filter | | | |
|---|---|---|---|---|
| | Group I | Group II | Group III | Group IV |
| Immunization | | | | |
| 2nd booster | 9.3 | 10.3 | 10.3 | 9.3 |
| 3rd booster | 12.3 | 12.3 | 13.3 | 12.3 |
| 4th booster | 13.3 | 13.3 | 14.3 | 14.3 |

| | DAc-SP5 (3 times per week, s.c.) | | | |
|---|---|---|---|---|
| Days After Last Booster | Group I[2] 10 µg/kg | Group II[2] 100 µg/kg | Group III[2] 500 µg/kg | Control Group IV |
| 7 | 13.6 ± 0.6 | 13.5 ± 0.7 | 13.6 ± 0.6 | 13.4 ± 0.5 |
| 14 | 13.5 ± 1.0 | 13.8 ± 0.8 | 13.8 ± 0.8 | 13.0 ± 0.8 |
| 21 | 13.0 ± 0.4 | 12.6 ± 0.4 | 12.8 ± 0.5 | 12.7 ± 0.5 |
| 28 | 12.9 ± 1.3 | 12.9 ± 0.8 | 13.0 ± 1.0 | 13.0 ± 0.9 |
| 35 | 12.8 ± 0.5 | 13.2 ± 0.5 | 12.7 ± 0.5 | 12.9 ± 0.5 |
| 42 | 13.0 ± 0.6 | 13.1 ± 0.9 | 12.7 ± 0.5 | 12.9 ± 0.5 |
| 49 | 12.9 ± 0.7 | 13.1 ± 0.9 | 12.6 ± 0.6 | 12.6 ± 0.4 |
| 56 | 12.3 ± 0.4 | 12.6 ± 0.9 | 12.1 ± 0.9 | 12.1 ± 0.4 |
| | $\bar{x}$ ± S.D n = 10 | $\bar{x}$ ± S.D n = 10 | $\bar{x}$ ± S.D n = 10 | $\bar{x}$ ± S.D n = 10 |

[1] $F_1$ hybrid mice (Balb/c × C57 BL/6J) were immunized with 1 µg ovalbumin (emulsified in 1 mg of Al(OH)$_3$. The anti-ovalbumin titer was determined with the help of the passive, cutaneous anaphylaxis (Wyszotkowska et al., Int. Archs. Allergy appl. Immun. 72:16–21 (1983)) by means of dilution series of the serum of the individual animals.
[2] There was no statistically significant difference between the values of the experimental and control groups.

We claim:

1. A method of stimulating growth of lymphocytes and monocytes following suppression of the immune system comprising administering an amount of at least one acylated splenopentin effective for stimulating growth of lymphocytes and monocytes, said acylated splenopentin being selected from the group consisting of N.alpha-arg, N.epsilon-lys-diacetylsplenopenotin, N.alpha-arg-monoacetylsplenopentin and N.epsilon-lys-monoacetylsplenopentin.

2. The method of claim 1, wherein the supression of the immune system resulted from one of cytostatic and virostatic chemotherapy.

3. A method of stimulating growth of bone marrow stem cells following suppression of the immune system comprising administering an amount of at least one acylated splenopentin effective for stimulating growth of bone marrow stem cells, said acylated splenopentin being selected from the group consisting of N.alpha-arg, N.epsilon-lys-diacetylsplenopentin, N.alpha-arg-monoacetylsplenopentin and N.epsilon-lys-monoacetylsplenopentin.

* * * * *